United States Patent
Block et al.

(10) Patent No.: US 7,422,758 B2
(45) Date of Patent: Sep. 9, 2008

(54) SUSTAINED RELEASE VITAMIN COMPOSITION

(75) Inventors: Juergen Block, Werther (DE); Stefan Heim, Herrenberg (DE); Ralf Westerheide, Bielefeld (DE)

(73) Assignees: GlaxoSmithKline Consumer Healthcare GmbH & Co. KG, Buehl (Baden) (DE); Allphamed Pharbil Pharma GmbH, Gottingen (DE)

( * ) Notice: Subject to any disclaimer, the term of this patent is extended or adjusted under 35 U.S.C. 154(b) by 0 days.

(21) Appl. No.: 10/239,808

(22) PCT Filed: Mar. 21, 2001

(86) PCT No.: PCT/EP01/03192

§ 371 (c)(1),
(2), (4) Date: Jan. 16, 2003

(87) PCT Pub. No.: WO01/72286

PCT Pub. Date: Oct. 4, 2001

(65) Prior Publication Data

US 2003/0148992 A1    Aug. 7, 2003

(30) Foreign Application Priority Data

Mar. 27, 2000  (GB)  .............................. 0007419.5

(51) Int. Cl.
*A61K 9/14*   (2006.01)
*A61K 9/16*   (2006.01)
*A61K 9/26*   (2006.01)
*A61K 9/48*   (2006.01)
*A61K 9/54*   (2006.01)

(52) U.S. Cl. ............ 424/489; 424/451; 424/458; 424/464; 424/469; 424/490; 424/493; 424/494; 424/497

(58) Field of Classification Search ......... 424/490, 424/400, 489, 439
See application file for complete search history.

(56) References Cited

U.S. PATENT DOCUMENTS

| | | | |
|---|---|---|---|
| 3,939,259 A | | 2/1976 | Pescetti |
| 4,808,413 A | * | 2/1989 | Joshi et al. ............... 424/458 |
| 5,006,341 A | * | 4/1991 | Davis et al. .............. 424/442 |
| 5,049,394 A | * | 9/1991 | Howard et al. ............ 424/490 |
| 5,093,200 A | | 3/1992 | Watanabe et al. .......... 428/407 |
| 5,158,777 A | * | 10/1992 | Abramowitz et al. ....... 424/458 |
| 5,869,084 A | * | 2/1999 | Paradissis et al. ......... 424/439 |
| 6,004,582 A | * | 12/1999 | Faour et al. .............. 424/473 |
| 6,419,960 B1 | * | 7/2002 | Krishnamurthy et al. .... 424/490 |

FOREIGN PATENT DOCUMENTS

| | | |
|---|---|---|
| EP | 0 208 362 | 1/1987 |
| EP | 0 327 086 | 8/1989 |
| EP | 0 527 638 | 2/1993 |

* cited by examiner

*Primary Examiner*—S. Tran
(74) *Attorney, Agent, or Firm*—Dara L. Dinner; Theodore Furman; Charles M. Kinzig

(57) ABSTRACT

A therapeutic formulation in the form of a beadlet, suitable for oral administration and adapted to provide immediate and sustained release of therapeutic material. Each beadlet comprises an extruded-spheronized inner core containing at least one medicament e.g. a slow release vitamin, an outer layer containing at least one medicament e.g. a fast release vitamin and a controlled release coating between the inner core and the outer layer which coating controls the release of the inner core medicament.

15 Claims, No Drawings

SUSTAINED RELEASE VITAMIN COMPOSITION

The present invention relates to therapeutic formulations adapted to provide timed-release of therapeutic material. In particular the invention relates to a beadlet or pellet designed to release therapeutic material at different rate(s) after ingestion.

Beadlets and the like have been used in the manufacture of controlled release medicaments for some time. For example, Spansule® technology developed in the 1950's, and still used today, utilizes neutral particles which are coated and adapted to release material over a prolonged period of time. Such particles contain a sugar-based core in which therapeutic material may be incorporated directly or may be dusted or otherwise distributed over the particle surface. The particles are then coated with a suitable coating material such as a wax or laquer. Release of therapeutic material by disintegration of the coating is controlled by controlling the thickness of the coating or by varying the coating composition. Examples of therapeutic preparations consisting of particles coated with a disintegreatable coating are disclosed in U.S. Pat. No. 3,939,259 (Pescetti). The preparations are formed by placing a portion of uncoated particles containing a therapeutically active material in a revolving pan and contacting the particles with sufficient coating solution, namely a zein-shellac solution, to cover the pellets. The coating operation is repeated until the zein-shellac coat is of suitable thickness so as to resist disintegration for a selected period of time after ingestion. Groups of particles, having different coatings designed to disintegrate at different times, are combined in capsules or tablets so as to produce modified-release therapeutic preparations.

Similarly U.S. Pat. No. 4,808,413 (Squibb) discloses immediate and modified release formulations in the form of beadlets. The beadlets are formed by an extrusion process and are disclosed as containing a medicament, an organic carboxylic acid, a non-lipophilic non-fat binder and when the formulations are modified release formulations, sustained release properties are conferred by a coating layer. It is suggested that different beadlet types i.e. immediate release beadlets and modified release beadlets, may be physically mixed together and either filled into capsule shells or compressed into tablets.

Whilst the extruded beadlets of U.S. Pat. No. 4,808,413 (Squibb) are disclosed as having improved properties, such as improved hardness and lower friability, as compared with similarly sized 'non-pareil' or neutral particles e.g. of the kind disclosed in the Pescetti patent, there are disadvantages. For example, extruded beadlets (or sugar-based cores) with varying levels of coating are required in order to achieve controlled release, i.e. sustained and immediate release, of medicament. Mixing different beadlet types in a single tablet or capsule results in higher manufacturing costs and greater complexity in the manufacturing process. Problems associated with formulating controlled release formulations comprising multiple active ingredients and comparatively few excipients are not addressed in the prior art.

Similarly U.S. Pat. No. 5,158,777 (Squibb) discloses capsules containing two different types of beads in order to confer sustained and immediate release characteristics. In one option sustained release is achieved by preparing a single active-containing spheres, namely captopril-containing spheres, using extrusion/spheronization technology, and then coating said spheres with an enteric or delayed release coating. The beads are then combined with non-coated beads, to provide a formulation with sustained and immediate release characteristics. Thus use of a single type of modified release-containing beadlet and moreover the formulation of a system comprising a plurality of active ingredients is not envisaged in this prior art.

Accordingly the need exists for controlled or modified release therapeutic formulations, providing for both immediate and sustained release of therapeutic material and which provide for greater flexibility in designing modified-release profiles for a wide variety of therapeutic materials. Further, the formulations should be simple and economical to produce.

According to the present invention there is provided a therapeutic formulation in the form of a beadlet suitable for oral administration from which medicament is released at controlled rates, the beadlet comprising an extruded-spheronized inner core containing at least one modified, i.e. sustained, release medicament, an outer layer containing at least one immediate release medicament, and a pharmaceutically acceptable controlled-release coating between the inner core and the outer layer, which coating controls the release of the inner core modified release medicament.

By "medicament" is meant one or more biologically active agents.

A beadlet of the invention comprises an inner core containing medicament, uniformly distributed therethrough. The inner core forms the nucleus of the beadlet. An inner core is prepared suitably by extrusion and spheronization of a mass, e.g. a wet mass, containing medicament, a binder and any other desired excipient.

By "modified release" is meant that release of medicament from the beadlet is controlled such that plasma concentrations of medicament may be maintained for a relatively long period of time for example up to 9 hours. Release and absorption of modified release medicament may initiate in the stomach and be continued thereafter during passage of the beadlet through the digestive tract i.e. through the duodenum, the jejunum, the ileum and into the ascending colon, or alternatively may initiate in the lower part of the intestine. Release and absorption initiated in the stomach is suitably achieved in beadlet forms comprising a diffusion-based pharmaceutically acceptable controlled-release coating whereas release and absorption initiated in the intestine is suitably achieved in beadlet forms comprising an enteric-based pharmaceutically acceptable controlled-release coating.

In vitro dissolution testing methods well known in the art, such as described in the European Pharmacopoeia and the USP may be used to determine release rate profiles of beadlets of the invention. Suitably at least 20% of the delayed release i.e the modified release medicament is released after 2 hours preferably at least 60% is released after 4 hours and even more preferably at least 80% of the delayed i.e. modified release medicament is released after 9 hours as determined by the dissolution test for solid dosage forms as described in the European Pharmacopoeia 1997, $3^{rd}$ Edition page 128, 2.9.3.

A beadlet of the invention contains an outer layer comprising a film-forming agent and medicament. The outer layer surrounds the pharmaceutically-acceptable coating in the beadlet. Medicament located in the outer layer of a beadlet is intended for immediate release.

By "immediate release" is meant that medicament is released relatively fast as compared with release of the modified release medicament. Release and absorption of the immediate release medicament occurs primarily in the stomach, although this will depend on the retention time of the beadlet in the stomach, which may vary according to whether the stomach is in the fed or fasted state. A therapeutically active plasma concentration of the immediate release medicament may be obtained within a relatively short period of time, for example 0.5-1 hour, following oral administration of a dosage form containing beadlets of the invention. Substantially all of the immediate release medicament is released from a beadlet at substantially the same time. Suitably at least 80%, preferably at least 90% and even more preferably at least 95% of the immediate release medicament is released within 1 hour as determined by the dissolution test for solid dosage forms as described in the European Pharmacopoeia 1997, 3$^{rd}$ Edition page 128, 2.9.3.

Beadlets of the invention are provided with a pharmaceutically acceptable controlled release coating or layer to mediate the controlled release of the inner core medicament from the beadlet. Advantageously the pharmaceutically acceptable controlled release coating may also provide an effective barrier between the inner core and the outer layer such that any potentially disadvantageous interaction between components therein is minimized.

Each beadlet of the invention provides for both immediate and sustained release of therapeutic material. Advantageously this obviates the need for different beadlet types conferring different medicament release rates, e.g. beadlets containing varying amount(s) of coating material, to be incorporated within a single tablet or capsule, although such beadlet types can nonetheless be used in combination with beadlets of the invention, if desired. Use of modified release beadlets according to the present invention result in time and cost savings compared with use of known beadlets requiring different levels of coating.

Unlike the neutral particles of the prior art, beadlets of the present invention are not based on an excipient core; consequently, a relatively large proportion of the beadlet may be taken up with modified release medicament or with immediate release medicament. Advantageously use of relatively small amounts of excipient allows comparatively larger amounts of medicament to be used without resulting in the production of larger-sized beadlets as compared with other particle or beadlet-based formulations containing the same amount of medicament. Such formulations of the prior art would result in the need for bigger tablets or capsules, which are more difficult to swallow and less likely to be favoured by the user. This problem is avoided in dosage forms according to the invention since equivalent amounts of medicament are contained in relatively smaller beadlets. This feature of the invention is particularly useful not only when a high dose of medicament is required but also when using a multi-component formulation comprising a plurality of active ingredients such as may be required in a multivitamin formulation. For example a formulation, intended for use in a nutritional supplement product, may contain as modified release medicament at least five vitamins e.g. 5 to 10, and/or at least two minerals e.g. 2 to 5, and/or at least five trace elements e.g. 5 to 12, and as immediate release medicament at least two vitamins, e.g. 2 to 5, and/or at least two minerals e.g. 2 to 5, and/or at least two trace elements e.g. 2 to 10.

Suitably the modified release medicament is present in an amount ranging from 5 to 95% by weight of the formulation, such as 5 to 15% by weight of the formulation, preferably 10 to 90% by weight of the formulation such as 40 to 60% by weight of the formulation, even more preferably 70 to 85% by weight of the formulation. Suitably the immediate release medicament is present in an amount ranging from 0.001 to 90% by weight of the formulation, such as 0.001 to 1% by weight of the formulation, preferably 0.1 to 50% by weight of the formulation even more preferably 0.15 to 30% by weight of the formulation. Immediate release medicaments in the range e.g. 10 to 20% by weight of the formulation are also encompassed in the beadlets of the invention.

The modified and immediate release medicament utilized in the present invention is not critical and may be selected from a wide variety of therapeutic materials which are orally administered, for example vitamins, minerals, trace elements, carotinoids, sedatives, somniferics, analgesics, antibacterial agents, decongestants and other drugs such as drugs for preventing and treating nicotine addiction e.g nicotine and its derivatives. Preferably the modified release medicament comprises one or more vitamins including carotinoids (carotene), trace elements or minerals or mixtures thereof. Suitably the vitamins include water-soluble vitamins e.g. Vitamin C e.g. L-(+)-ascorbic acid, calcium ascorbate, potassium ascorbate, 6-palmitoyl-L-ascorbic acid; Vitamin B1 e.g. thiamine hydrochloride, thiamine mononitrate; Vitamin B2 e.g. riboflavin, riblflavin 5'-phosphate sodium; Vitamin B6 e.g. pyridoxine hydrochloride, Vitamin B12 e.g. cyanocobalamine; Vitamin H e.g. D-biotin; Folic Acid; Vitamin PP (Niacin) e.g. nicotinamide, nicotinic acid; pro-Vitamin B5 e.g. panthenol (D and DL forms) ethyl panthenol and calcium D-pantothenate; and fat-soluble vitamins e.g. Vitamin A e.g. Vitamin A palmitate, Vitamin A acetate Vitamin A propinate, all trans retinol; Vitamin D e.g. ergocalciferol, cholecaciferol, cholecaciferol-cholesterol; Vitamin E e.g. alpha-tocopherol, alpha-tocopheryl acetate, alpha-tocopheryl acid succinate (d and dl forms); Vitamin K such Vitamin K1 e.g. phytomenadione, and Carotene (pro-vitamin) e.g. lycopin, zeaxanthin, lutein, alpha-carotene, beta-carotene, apocarotinal, gamma carotene and beta cryptoxanthin. Preferably the modified release medicament is a mixture of vitamins e.g. a mixture of water-soluble vitamins or a mixture of fat-soluble vitamins or a mixture of water-soluble and fat-soluble vitamins, as described above. When the vitamin or vitamin mixture comprises riboflavin, it is particularly preferred to use a salt form such as riboflavin phosphate. Surprisingly it has been discovered that this form of the vitamin imparts greater stability to the formulation as compared with other commercially available forms.

Suitable trace elements include the elements in salt form i.e. both inorganic salts and organic salts, when available. Examples include iron e.g. iron fumarate, iron citrate, iron lactate; zinc e.g. zinc lactate, zinc citrate, zinc oxide; iodine e.g. sodium iodate, potassium iodide; copper e.g. copper gluconate, copper sulphate; manganese e.g. manganese citrate, manganese sulphate; molybdenum e.g. sodium molybdate, ammonium molybdate; selenium e.g. sodium selenate, sodium selenite; chromium e.g. chromium chloride, chromium citrate; silicates e.g. silicon dioxide, sodium silicate; and flouride e.g. sodium fluoride. Suitable examples of minerals include calcium e.g. calcium hydrogen phosphate, calcium citrate; magnesium e.g. magnesium carbonate, magnesium lactate; potassium e.g. potassium chloride, potassium sulphate; phosphorus e.g. calcium phosphate; and chloride e.g. potassium chloride, magnesium chloride.

The immediate release medicament may be the same or a different chemical entity to the modified release medicament; preferably it is different. Suitably the immediate release medicament is material that is not well absorbed in slow release form; for example a vitamin such as folic acid or Vitamin B12 (cyanocobalamine). Suitably the immediate release medicament comprises one or more vitamins, minerals, carotinoids or trace elements or mixtures thereof. Suitable vitamins include carotinoids (carotene), fat soluble vitamins and water soluble vitamins as hereinbefore described;

folic acid and Vitamin B12 are preferred immediate release vitamins. Suitable trace elements and minerals include those hereinbefore described.

Suitably a single dose of a multitivitamin formulation according to the invention will contain an amount of each vitamin ranging from 10% to 300%, preferably from 100% to 250% of the recommended daily allowance (RDA), and a nutritionally supplemental amount of minerals and trace elements, for example ranging from 1 to 100% RDA.

Advantageously combinations of different therapeutic materials, including those that are usually incompatible with each other, may be incorporated in a single beadlet of the invention. In the latter case, the incompatible therapeutic materials are kept apart from each other for example a first material may be in the inner core whilst a second material, incompatible with the first, may be in the outer layer. For example when the modified release medicament includes fat-soluble vitamins, it is preferred that the modified release medicament does not include trace elements, as certain elements may be incompatible with fat-soluble vitamins. Thus it is preferred that the fat-soluble vitamins are contained in the inner core whilst the trace elements are contained in the outer layer.

Typically the pharmaceutically acceptable controlled release coating is a diffusion coating or an erodable coating such as an enteric coating, i.e. a coating that is substantially resistant under gastric conditions but is eroded during passage through the small intestine. Suitable coatings include shellac, cellulose acetate phthalate, hydroxy propyl methyl cellulose phthalate, ethyl cellulose and polymerizates of acrylic acid esters and methacrylic acid esters like e.g. Eudragit® RS. Eudragit® L is a suitable enteric coating material. Eudragit® coating materials are available from Rohm Pharma. Shellac, a diffusion coating, is suitably obtained in one form as the purified product of the natural polymer Lac, the resinous secretion of the insect *Kerria Lacca*, Shellac is a preferred pharmaceutically acceptable controlled release coating. Suitably the pharmaceutically acceptable controlled release coating comprises 0.25 to 40% by weight of the composition, i.e. of the beadlet formulation, more suitably 0.5 to 20% and even more suitably 1 to 10% by weight of the composition.

The outer layer, containing the immediate release medicament, which substantially surrounds the pharmaceutically acceptable controlled release layer, is suitably applied to the coated inner cores in the form of an aqueous solution or a dispersion of a film-forming material. For example the dispersion may comprise a film-forming material selected from the group consisting of hydroxy propyl cellulose, hydroxy propyl methylcellulose, gum arabic, polyvinyl pyrrolidone, polyvinyl pyrrolidone-vinylacetate copolymer and copolymerisate of dimethyl amino methacrylic acid/neutral methacrylic acid esthers. An outer layer comprising a mixture of hydroxypropylcellulose and polyvinylpyrrolidone is preferred.

According to the invention the beadlets may optionally comprise a further coating, which further coating may be located between the inner core and the pharmaceutically acceptable controlled-release coating. Advantageously the further coating may serve to protect the content of the inner core from exposure to the pharmaceutically acceptable coating and to the surrounding atmosphere. Such further coating will also be pharmaceutically acceptable. It has been found that stability of formulations of the invention may be increased when the beadlets comprise a further coating. It is especially preferred to use a further coating when the beadlet, specifically the inner core, comprises Vitamin C and the pharmaceutically acceptable controlled-release coating comprises shellac, as the integrity of the shellac coating may be compromised by Vitamin C. Suitably the further coating may be selected from the group consisting of hydroxy propyl cellulose, hydroxy propyl methylcellulose, gum arabic, polyvinyl pyrrolidone, polyvinyl pyrrolidone-vinylacetate copolymer and copolymerisate of dimethyl amino methacrylic acid/neutral methacrylic acid esthers. A further coating comprising a mixture of hydroxypropylcellulose and polyvinylpyrrolidone is preferred.

Beadlets of the invention may further comprise a plasticizer e.g. glycerol, polyethylene glycol, castor oil and acetylated monoglycerides; a pH modifier such as potassium hydrogenphosphate, a filler such as e.g. calcium carbonate, a binding agent such as microcrystalline cellulose. Other, non-limiting examples of excipients include stabilizers, lubricants, blasting agents and colorants.

Suitably beadlets of the invention are prepared by forming the inner core by mixing and kneading with a suitable solvent, for example in a conventional blender, the modified release medicament(s) and any excipients, including a binder, to form a wet mass. A solvent or solvent mixture is used in an amount to enable a wet mass of appropriate consistency to be formed; typically 5 to 40% by weight of the dry mass is used. Suitable solvents include for example polar solvents such as lower alcohols e.g. methyl alcohol, ethyl alcohol, isopropyl alcohol; ketones e.g. acetone or ethylmethyl ketone; chlorinated hydrocarbons e.g. methylene chloride, dichloroethane and 1,1,1-trichloroethane. Thereafter the wet mass is extruded, for example employing a standard extruder e.g. a Nica or Luwa or other type of extruder, to form an extrudate which is then passed through spheronizing equipment to convert the extrudate into inner cores of appropriate particle size range. Suitably spheres produced by the spheronization process are substantially uniform spherical particles, typically having a diameter in the range 0.8 to 2.2 mm, preferably 1.0 to 2.0 mm. The cores may be dried by tray drying, oven or fluid bed drying. The cores are then coated with a solution or dispersion of the pharmaceutically acceptable controlled release coating. When present, the further coating is applied before applying the pharmaceutically acceptable controlled-release coating. The pharmaceutically acceptable controlled-release coating and the further coating may be applied by pan coating, fluid bed coating or the like. The outer layer containing the immediate release medicament is then applied so as form the complete beadlet, e.g. in aqueous solution or as a dispersion of film-forming materials e.g. of the type suitable for forming the further coating. Beadlets obtainable by the process described hereinabove form another aspect of this invention.

In a further aspect of the invention there is provided a method for time-specific delivery of a therapeutically active agent to a patient in need thereof, said method comprising administering to said patient, an oral dosage form containing a plurality of beadlets from which medicament is released at controlled rates, the beadlets comprising an inner core containing at least one modified release medicament, an outer layer containing at least one immediate release medicament, and a pharmaceutically acceptable controlled-release coating between the inner core and the outer layer, which coating controls the release of the inner core modified release medicament, and wherein the inner core is provided by extrusion of a wet mass of material containing modified release medicament followed by spheronization of the extrudate.

Beadlets of the invention are suitable for oral administration and may be filled into capsules, e.g. hard shell capsules, or compressed into tablets to provide compositions to be administered in single or divided doses.

A further object is to provide an oral dosage form such as a tablet or a capsule containing a plurality of beadlets of the invention. Advantageously, beadlet formulations of the invention may be accomodated in standard sized capsules e.g. size 0 and size 1 capsules, even when beadlets comprise multi-component formulations such as multivitamin formulations.

It will also be understood that beadlets containing one or more therapeutic agents may be physically mixed with other beadlets containing one or more of the same or different beadlets for filling in capsule shells or compressing into tablets. Each beadlet may contain at least one medicament which may be the same or different from medicament contained in another beadlet.

Dosage forms of the invention may be suitable for use as pharmaceuticals or as nutritional supplements, for example multivitamin preparations.

The invention is disclosed in further detail in the following examples which should not be construed as limiting the invention in any way.

EXAMPLE 1:

| Vitamin C plus Vitamin B-Complex Pellet: | mg/capsule |
| --- | --- |
| Ascorbic acid* | 150.0000 |
| Nicotinamide* | 45.0000 |
| Calcium pantothenate* | 16.3000 |
| Pyridoxine hydrochloride* | 6.0400 |
| Riboflavin phosphate* | 4.0000 |
| Thiamine nitrate* | 4.2900 |
| Cyanocobalamine | 0.0025 |
| Folic acid | 0.5000 |
| Biotin* | 0.3750 |
| Microcrystalline cellulose | 126.1532 |
| Stearic acid | 21.1893 |
| Schellac | 28.0352 |
| Glycerol | 0.3425 |
| Klucel (Hydroxypropyl cellulose) | 4.1359 |
| Potassium hydrogen phosphate | 10.5423 |

*sustained release component

Method of Preparation

All components are weighed and dry mixed. Prior to mixing, selected components are premixed so as to help ensure homogeneity of the final mixture. Biotin and potassium hydrogen phosphate are premixed with approximately 50% of the ascorbic acid. Nicotinamide, calcium pantothenate, pyridoxine hydrochloride, riboflavin phosphate, thiamine nitrate, stearic acid and microcrystalline cellulose are premixed with the remainder of the ascorbic acid. Both of the premixed mixtures are then combined and mixed further to form the inner core mixture, which is then kneaded using isopropyl alcohol to form a wet mass. The wet mass is passed through a PP127 (Schluter) extruder (~0.05-0.10 mm koller space). The extrudate is then passed through an RM700 (Schluter) spheronizer to form the beadlet cores. The spheronized mixture is then dried in a fluid bed drier at 55° C. over a period of approximately 45 minutes. The beadlet cores are cooled to above ambient temperature, i.e. 30-35° C., and are then sieved. The sieved beadlets are heated to approximately 40° C. in a fluid bed coater. A solution of Klucel (hydroxypropyl cellulose) in ethanol is applied by spraying until the cores are suitably coated with the Klucel. The coated cores are then dried for a short period of time e.g. for ten minutes or so. Shellac, diluted in a water/glycerol (179:1) mixture is then sprayed onto the cores. Samples of the shellac-coated cores may be removed for analysis during the coating process e.g. to determine release rates. When the desired release rate, and accordingly the required level of coating, has been achieved an additional solution of Klucel containing folic acid and cyanocobalamin is sprayed on to the coated cores. The beadlets formed are sieved and filled into hard shell gelatin capsules.

EXAMPLE 2:

| Vitamin B-Complex Pellet: | Mg/capsule |
| --- | --- |
| Nicotinamide* | 27.0000 |
| Calcium pantothenate* | 9.7800 |
| Pyridoxin hydrochloride* | 3.6240 |
| Riboflavin phosphate* | 2.4000 |
| Thiamine nitrate* | 2.5740 |
| Cyanocobalamine | 0.0015 |
| Folic acid | 0.3000 |
| Biotin* | 0.2250 |
| Microcrystalline cellulose | 145.2982 |
| Stearic acid | 17.3965 |
| Schellac | 20.9800 |
| Glycerol | 0.5985 |
| Calcium hydrogen phosphate | 235.7520 |
| Potassium hydrogen phosphate | 7.2351 |

*sustained release component

Method of Preparation

Premixes of selected components are prepared. Biotin and potassium phosphate are premixed with approximately 50% of the available microcrystalline cellulose and calcium hydrogen phosphate. Another premix is formed containing nicotinamide, calcium pantothenate, pyridoxine hydrochloride, riboflavin phosphate, thaimine nitrate, stearic acid and the remainder of the microcrystalline cellulose and calcium hydrogen phosphate. The premixed mixtures are combined and beadlets are formed as described above, with the exception that the shellac coat is applied directly to the extruded cores. The beadlets formed are filled into hard-shell gelatin capsules.

The invention claimed is:

1. An oral therapeutic formulation in the form of a beadlet comprising:
   a) an extruded-spheronized inner core containing at least one modified release first medicament selected from one or more vitamins, trace elements or minerals or mixtures thereof;
   b) an outer layer containing film forming agent selected from hydroxy propyl cellulose, hydroxypropylmethylcellulose, gum arabic, polyvinyl pyrrolidone, polyvinyl pyrrolidone-vinylacetate copolymer, copolymerisate of dimethyl amino methacrylic acid/neutral methacrylic acid esters or a mixture thereof, and containing at least one immediate release second medicament selected from one or more vitamins, trace elements or minerals or mixtures thereof;
   wherein the immediate release second medicament is a different chemical entity to the modified release first medicament;
   c) a pharmaceutically acceptable controlled-release first coating layer between the inner core and the outer layer, which coating controls the release of the inner core modified release first medicament and which first coating layer is selected from shellac, cellulose acetate phthalate, hydroxy propyl methyl cellulose phthalate, ethyl cellulose and polymerisates of acrylic acid esters or methacrylic acid esters; and d) a second coating layer between the inner core and the first coating layer of a pharmaceutically acceptable controlled release coating selected from hydroxy propyl cellulose, hydroxy propyl methylcellulose, gum arabic, polyvinyl pyrrolidone, polyvinyl pyrrolidone-vinylacetate copolymer and copolymerisate of dimethyl amino methacrylic acid/neutral methacrylic acid esters, or a mixture thereof.

2. The therapeutic formulation according to claim 1 wherein the pharmaceutically acceptable controlled-release first coating layer is shellac.

3. The therapeutic formulation according to claim 2 wherein the pharmaceutically acceptable controlled-release first coating layer comprises 0.25 to 40% by weight of the composition.

4. The therapeutic formulation according to claim 3 wherein the pharmaceutically acceptable controlled-release first coating layer comprises 0.5 to 20% by weight of the composition.

5. The therapeutic formulation according to claim 3 wherein the pharmaceutically acceptable controlled-release first coating layer comprises 1 to 10% by weight of the composition.

6. The therapeutic formulation according to claim 1 wherein the second coating is a mixture of hydroxypropylcellulose and polyvinylpyrrolidone.

7. The therapeutic formulation according to claim 1 wherein the outer layer comprises a mixture of hydroxypropylcellulose and polyvinylpyrrolidone.

8. The therapeutic formulation according to claim 1 wherein the modified release first medicament is a fat-soluble vitamin.

9. The therapeutic formulation according to claim 8 wherein the immediate release second medicament is a trace element.

10. The therapeutic formulation according to claim 1 wherein the immediate release second medicament comprises one or more vitamins, minerals, carotinoids or trace elements or mixtures thereof.

11. The therapeutic formulation according to claim 10 wherein the vitamin is selected from folic acid, Vitamin B12 (cyanocobalamine), carotinoids (carotene), fat soluble vitamins and water soluble vitamins.

12. The therapeutic formulation according to claim 1 wherein the modified release first medicament comprises one or more vitamins selected from carotinoids (carotene), L-(+)-ascorbic acid, calcium ascorbate, potassium ascorbate, 6-palmitoyl-L-ascorbic acid, Vitamin B1 e.g. thiamine hydrochloride, thiamine mononitrate, Vitamin B2, riboflavin, riblflavin 5'-phosphate sodium, Vitamin B6, pyridoxine hydrochloride, Vitamin B12, cyanocobalamine, Vitamin H, D-biotin; Folic Acid, Vitamin PP (Niacin), nicotinamide, nicotinic acid; pro-Vitamin B5, panthenol (D and DL forms) ethyl panthenol, calcium D-pantothenate, Vitamin A, Vitamin A palmitate, Vitamin A acetate Vitamin A propinate, all trans retinol, Vitamin D , ergocalciferol, cholecaciferol, cholecaciferol-cholesterol, Vitamin E, alpha-tocopherol, alpha-tocopheryl acetate, alpha-tocopheryl acid succinate (d and dl forms), Vitamin K, Vitamin K1, phytomenadione, lycopin, zeaxanthin, lutein, alpha-carotene, beta-carotene, apocarotinal, gamma carotene and beta cryptoxanthin.

13. The therapeutic formulation according to claim 12 wherein the modified release first medicament comprises a mixture of water-soluble vitamins, a mixture of fat-soluble vitamins, or a mixture of water-soluble and fat-soluble vitamins.

14. The therapeutic formulation according to claim 1 wherein the trace elements are selected iron fumarate, iron citrate, iron lactate, zinc lactate, zinc citrate, zinc oxide, sodium iodate, potassium iodide, copper gluconate, copper sulphate, manganese citrate, manganese sulphate, sodium molybdate, ammonium molybdate, sodium selenate, sodium selenite, chromium chloride, chromium citrate, silicon dioxide, sodium silicate, sodium fluoride, and mixtures thereof.

15. The therapeutic formulation according to claim 1 wherein the minerals are selected from calcium hydrogen phosphate, calcium citrate, magnesium carbonate, magnesium lactate, potassium chloride, potassium sulphate, calcium phosphate, potassium chloride, and magnesium chloride, or mixtures thereof.

* * * * *